(12) United States Patent
Ehwald et al.

(10) Patent No.: US 7,892,857 B2
(45) Date of Patent: Feb. 22, 2011

(54) ASSAY BY OSMOTICALLY INDUCED SEPARATION AND CONCENTRATION OF HIGH-MOLECULAR DETECTABLE SUBSTANCES AND A FLUID MICROSYSTEM FOR CARRYING OUT SAID ASSAY

(76) Inventors: Rudolf Ehwald, Strelitzer Strasse 56, Berlin (DE) 10115; Helge Adleff, Bernhard-Lichtenberg-Strasse 3, Berlin (DE) 10407; Frank Bier, Jägersteig 12, Potsdam (DE) 14482; Nenad Gajovic-Eichelmann, Marathonaflee 20, Berlin (DE) 14052; Max Ehwald, Dietenhofer Strasse 11, Berlin (DE) 10405

( * ) Notice: Subject to any disclaimer, the term of this patent is extended or adjusted under 35 U.S.C. 154(b) by 433 days.

(21) Appl. No.: 11/847,495

(22) Filed: Aug. 30, 2007

(65) Prior Publication Data
US 2008/0038845 A1    Feb. 14, 2008

Related U.S. Application Data

(63) Continuation of application No. PCT/EP2006/001873, filed on Mar. 1, 2006.

(30) Foreign Application Priority Data
Mar. 4, 2005    (DE) ................... 10 2005 010 096

(51) Int. Cl.
*G01N 33/00*    (2006.01)
*G01N 33/48*    (2006.01)
*G01N 33/50*    (2006.01)
*G01N 33/53*    (2006.01)
*G01N 33/531*   (2006.01)
*G01N 33/533*   (2006.01)
*G01N 33/534*   (2006.01)
*G01N 33/535*   (2006.01)
*G01N 33/536*   (2006.01)
*G01N 33/537*   (2006.01)
*G01N 21/00*    (2006.01)
*B01L 3/00*     (2006.01)

(52) U.S. Cl. ............ 436/536; 422/68.1; 422/71; 422/82; 422/82.01; 422/82.05; 422/100; 422/101; 422/102; 422/103; 435/4; 435/7.1; 435/7.9; 435/287.2; 435/288.2; 435/288.5; 435/288.7; 435/968; 436/501; 436/504; 436/542; 436/149; 436/164

(58) Field of Classification Search ............... None
See application file for complete search history.

(56) References Cited

U.S. PATENT DOCUMENTS 5,045,193 A    9/1991  Pinon (Continued)

FOREIGN PATENT DOCUMENTS

DE    19729492 A1    10/1997

(Continued)

*Primary Examiner*—Unsu Jung

(57) ABSTRACT

The invention relates to an assay method and a fluid microsystem for carrying out said assay method, in particular, for carrying out miniaturized affinity tests in a micro-array format. According to said invention, a liquid phase comprising at least one type of detectable high-molecular weight soluble substance, for example a labeled reaction partner or product of an affinity reaction is displaced by the hydraulic effect of a high-molecular weight osmotic agent on an ultrafiltration membrane towards a miniaturized measuring chamber defined thereby. The fraction of the detectable high-molecular weight substance(s) is concentrated in the measuring chamber, while the dissolved low-molecular weight components are removed with the solvent through the membrane pores, thereby making it possible to attain a high detection sensitivity.

10 Claims, 2 Drawing Sheets

U.S. PATENT DOCUMENTS

| | | |
|---|---|---|
| 5,770,086 A | 6/1998 | Indriksons |
| 5,894,061 A | 4/1999 | Ladouceur |
| 2002/0086309 A1 * | 7/2002 | Benn et al. .................... 435/6 |
| 2002/0106787 A1 | 8/2002 | Benn |

FOREIGN PATENT DOCUMENTS

| | | |
|---|---|---|
| DE | 10134860 A1 | 2/2003 |
| DE | 10311622 A1 | 10/2004 |
| WO | WO-02/15949 A2 | 2/2002 |

* cited by examiner

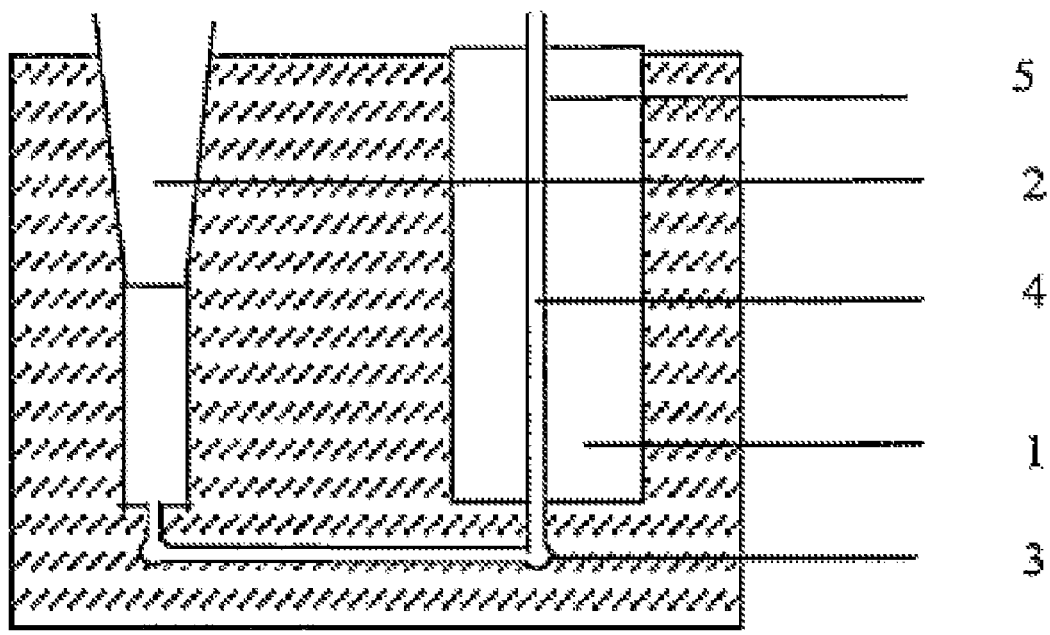
Fig. 1A
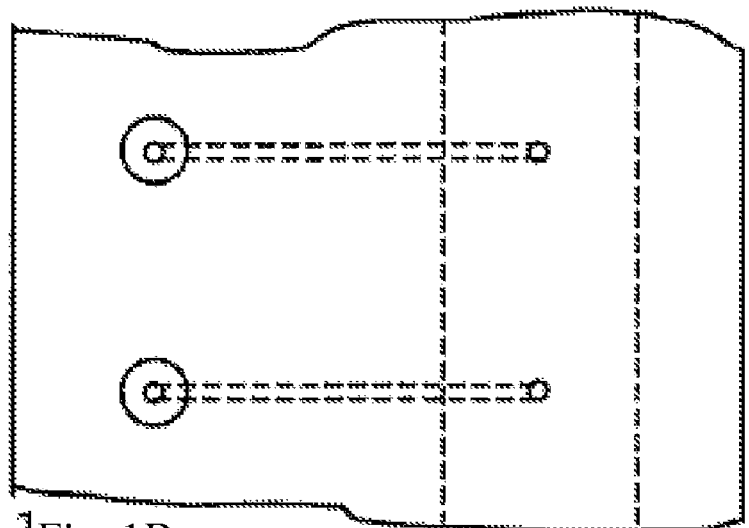
Fig. 1B
Fig. 1

ASSAY BY OSMOTICALLY INDUCED SEPARATION AND CONCENTRATION OF HIGH-MOLECULAR DETECTABLE SUBSTANCES AND A FLUID MICROSYSTEM FOR CARRYING OUT SAID ASSAY

CROSS REFERENCE TO RELATED APPLICATIONS

This is a continuation application of international PCT application No. PCT/EP2006/001873 which was filed on Mar. 1, 2006, published as publication No. WO 2006/092293 on Sep. 8, 2006, and claims priority from German application No. 10 2005 010 096.1 filed Mar. 4, 2005; both of which are incorporated herein by reference in their entirety.

BACKGROUND OF THE INVENTION

Affinity assays are analytical methods based on non-covalent affinity binding. Among them are immune tests or resp. immunoassays which happen to be standard operations in clinical chemistry, diagnostics, environmental analytics and bio-process control. The basis of any affinity assay is at least one specific perception reaction, for instance the specific binding of an affinity ligand to an antibody. Instead of immune-proteins, also other affinity receptors like lectines or aptamers, can be used for selective binding to an analyte.

Inherent specificity and high affinity of affinity binding enables selective, highly specific and highly sensitive concentration measurement. By means of antibodies, it is possible to record picomolar or nanomolar solutions of numerous analytes. Specific antibodies can be produced for almost all kinds of chemical compounds, from low-molecular weight substances, so-called haptenes, up to biological or synthetic macromolecules. Methods of establishing and implementation of affinity assays are well known in professional circles and can be read in a large number of publications (by example James P. Gosling "Immunoassays", Practical Approach Series, Oxford University Press, Oxford, UK).

An immunoassay or affinity assay normally consists of several steps, a.o. at least one incubation step, at least one washing step and a concentration measurement.

Modern techniques have been developed over the last years, which simplify the handling of immunoassays and thus making them accessible to new applications such as the pregnancy test in a control strip format (immunochromatography). Another direction of development is to incorporate a multitude of immune tests on a small area, the "Biochip" or "Microarray". Some immune tests in microarray format have the ability to detect a multitude of analytes from a single blood sample. One of the problems related to miniaturization of immunoassays consists in decrease of signal strength by reduction of reagent amount.

Since the common affinity receptors (e.g. antibodies and antigens) and their binding partners are not directly detectable in a sensitive way by usual detectors, they are chemically linked to a labeling substance ("label" or "marker") providing a detectable signal depending on analyte concentration. For miniaturized immunoassays, labels of the most specific activity are required, e.g. enzymes (a. o. peroxidase, alkalic phosphatase) or fluorescent dyes with high fluorescence recovery rates. Using enzymes, an amplification is achieved by catalyzing the generation of a signal substance (e.g. a colored reaction product). Fluorescent dyes allow the fastest and most direct detection, however, high sensitivity of fluorescence affinity assays requires extensive high-performance optical devices.

High-molecular weight antigens such as proteins can be detected in a particularly favorable way by a "sandwich"-immunoassay. In its most common implementation, the surface is coated by a specific antibody so that, after incubation with a sample solution, the analyte is linked to the surface, whereas other components of the sample are removed during a subsequent washing procedure. The actual detection takes place after incubation with a second, labeled specific antibody and yet another washing procedure (and, if necessary, a chromogenic reaction when using enzyme labels). The dose-effect correlation is positive.

The quantitative ascertainment of substances with a molecular weight below 1000 Dalton is one of the most important application fields of immunoassays. For these purposes, almost exclusively so-called competitive assays are applied. Here, the non-labeled analyte competes against an analog for the free binding places of an affinity receptor. The latter or the competing analog, which can be a high- or low-molecular weight soluble substance, carry the label.

In competitive affinity assays for the detection of low-molecular weight analytes, normally the labeled molecules are split into a soluble and a surface-bound fraction whereas the proportion of these fractions is dependent on the analyte concentration. Affinity binding of the labeled molecules to a surface coated with immobilized reactants takes place in many cases. The amount of surface-bound label is measured after flushing away the soluble fraction. In the absence of the competing analyte, the maximum amount of labeled molecules can be bound to the surface; the amount of surface-bound labeled molecules is reduced by the specific binding of the analyte to its receptor.

Since the amount of bound labeled substance is measured after a washing procedure, an inverse dose-effect correlation results, i.e. the strongest signals are attained at the lowest analyte concentrations; at very high analyte concentrations a low dependence of signal strength on concentration occurs, at very low analyte concentrations the uncertainty of the differential measurement is interfering. Due to the principle of difference measurement, the concentration of the labeled reactant has to be adjusted to that of the analyte. As the immobilized amount of labeled substance normally forms a very thin surface layer, detector performance requirements are high for small measuring areas, what has an impact on expenses.

It would be desirable either to overcome the inverse characteristics of competitive assays or to achieve a ratiometric measurement of the fraction of labeled molecules formed by the reaction with the analyte. The heterogeneous test system has the additional disadvantage of unavoidable unspecific binding of labeled molecules to the surface, thus causing more or less noise. It would be of great advantage, if competitive affinity assays could be carried out completely in homogeneous phase.

The mentioned limitations of competitive immunoassays mostly rely on the fact that only the surface-bound fraction of the labeled binding partner (e.g. of the antibody or the antigen) is being detected. At present, there is a strong requirement for miniaturized immunoassays with positive dose-effect correlation and/or without the necessity of linking the labeled molecules to a surface.

BRIEF SUMMARY OF THE INVENTION

The invention relates to an assay method and a fluid microsystem for carrying out said assay method, in particular, for carrying out miniaturized affinity tests in a micro-array format. According to the present invention, a liquid phase is displaced by the hydraulic effect of a high-molecular weight osmotic agent on an ultrafiltration membrane towards a miniaturized measuring chamber defined thereby. The liquid phase is comprising at least one type of detectable high-molecular weight soluble substance, for example a labeled reaction partner or product of an affinity reaction. The fraction of the detectable high-molecular weight substance(s) is concentrated in the measuring chamber, while the dissolved low-molecular weight components are removed with the solvent through the membrane pores, thereby making it possible to attain a high detection sensitivity. A positive signal can be obtained in the competitive mode or an assay can be carried out in homogeneous phase. Low expenditure of time and human labor for carrying out said assay method is another advantage.

BRIEF DESCRIPTION OF THE SEVERAL VIEWS OF THE DRAWINGS

FIG. 1 illustrates a cross section and a topview of a variant of the fluidic microsystem according to the present invention. Shown is a section of an aspiration chamber (1), filling chambers (2), flow paths (3), measuring chambers (4), and ultrafiltration membranes (5), which are implemented as capillary ultrafiltration membranes here.

DETAILED DESCRIPTION OF THE INVENTION

Figure 2:
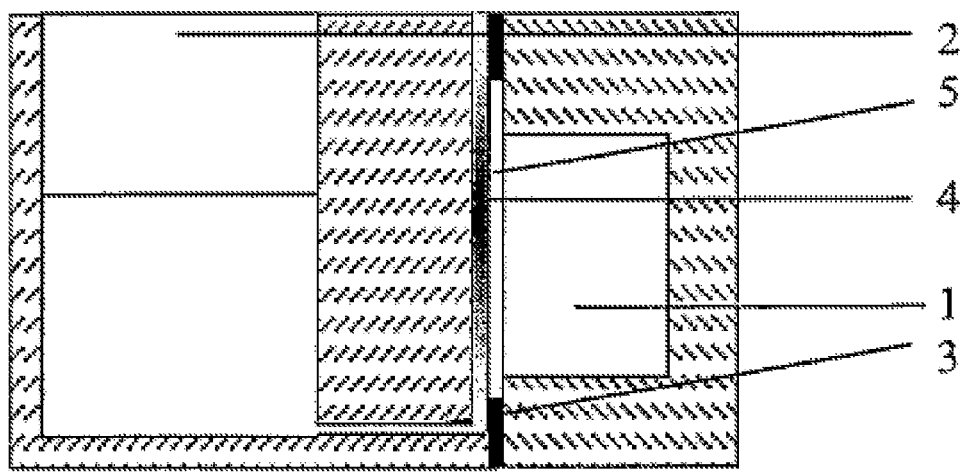
FIG. 2 illustrates a cross section of an other variant of the fluidic microsystem according to the present invention, whereas the ultrafiltration membrane (5) is implemented as a flat membrane.

It is an object of the present invention to provide a new, cost-efficient and highly sensitive method and an according appliance for the realization of quantitative, particularly competitive assays, preferably affinity assays, in single- or microarray-format. The method according to the present invention should provide the opportunity for a positive dose-effect correlation after a convenient and standardized separation of the fractions of labeled molecules produced by the reaction with the analyte. Said method should be realizable without binding the labeled molecules to a surface. In addition said method should enable increased sensitivity in comparison to common methods.

According to the present invention the object is achieved by an assay according to claim 1 and a fluidic micro-system according to claim 12. Advantageous embodiments of the invention are itemized in subclaims 2-11 and 13-16.

The nature of the present invention consists in the utilization of macromolecular osmolytes and ultrafiltration membranes for the concentration of high-molecular weight substances to be detected and the separation of said high-molecular weight substances from potentially interfering low-molecular weight substances.

In the case of an affinity assay typically the fractions of the labeled molecules resulting from the reaction with the analyte have to be separated and their concentrations have to be determined.

With affinity assays, usually a sample matrix to be analyzed, including labeled and unlabeled reactants, is mixed. Subsequently, the labeled reactant, due to affinity binding with the analyte or competition against the analyte for affinity binding, exists in different binding types (e.g. soluble/insoluble or complex-bound/not complex-bound). The ratio of said binding types is dependent on the concentration of the analyte.

A precondition for an affinity assay according to the present invention is to carry out the reaction of the analyte with the reactants in a way that afterwards only one fraction occurs in both, soluble and high-molecular form. To achieve this, various options are known among experts.

A non-restricting example is the binding of a low-molecular weight label, representing a labeled analog to the analyte, to a receptor, e.g. an antibody. After the reaction, in this case one fraction of the labeled analog is a high-molecular weight species and the other is of low-molecular weight. Further examples are the competition of the analyte against a labeled soluble high-molecular weight analog for binding sites of an immobilized antibody and the competition of the analyte against an immobilized analog of a labeled insoluble antibody. In both cases, labeled macromolecules exist in dissolved and undissolved form after the reaction; their concentration depending on the concentration of the analyte.

According to the present invention, the terms "high-molecular weight" and "low-molecular weight" are understood in comparison to the pore size of an ultrafiltration membrane applied according to said invention. This means that a low-molecular weight fraction can pass the applied membrane in a relatively unhindered way (reflection coefficient <0,5), whereas the high-molecular weight fraction can hardly permeate (reflection coefficient near 1).

Adequate ultrafiltration membranes of capillary or planar shape with a molar weight cut-off (referring to proteins) between 5,000 and $10^6$, and molecular size cut-off (referring to the stokes' diameter) between 1.5 and 50 nm respectively, are on offer by various manufacturers. Typical but not restricting ranges of molecular weight and molecular size for low-molecular weight substances are below 5 kDa resp. below 2 nm, the ones for high-molecular weight substances being above 10 kDa resp. above 3 nm. Since labeled affinity binding partners of various molecular size in the range between 0.3 and 50 nm are commercially available or can be prepared, the critical molecular size in order to distinguish the low-molecular weight fraction from the high-molecular weight fraction can be adapted to the available reactants by choosing the appropriate membrane. Application of a membrane with a very high molecular size cut-off has the advantage of a high hydraulic permeability but requires accordingly high molecular size of the labeled reactant or product and osmoticum.

According to the present invention, the liquid phase, including the soluble fraction of high molecular weight to be detected, is moved by the hydraulic effect of a high-molecular weight osmoticum on an ultrafiltration membrane (5) from a larger filling chamber (2) through a flow path (3) into a smaller measuring chamber (4) after a concentrated solution of the polymer osmoticum is filled into an aspiration chamber (1) (see FIGS. 1 and 2).

According to the present invention, the terms "flow path" and "capillary flow path" respectively, are understood as a hydraulic connection between the filling chamber and the measuring chamber, the total volume of said path and measuring chamber representing only a small part of the volume of the filling chamber.

At an ultrafiltration membrane, separating the aspiration chamber from any measuring chamber, the high-molecular weight osmoticum causes an hydraulic effect on the liquid phase including the labeled reagent. The liquid is moved into the measuring chamber and its low-molecular weight components are soaked through the pores of the ultrafiltration membrane together with the solvent.

Basically it is worth considering every high-molecular weight substance as a high-molecular weight osmolyte, whose aqueous solution is characterized by an osmotic potential sufficiently lowered (as a general rule by more than 0.1 MPa). It is known that in particular concentrated solutions of hydrophilic polymers such as polyethylene oxide or polyvinyl alcohol, whose molecules can be described as strongly hydrous coils, show a strong osmotic force independent of their particle concentration. This is because the concentrated solutions represent network fluids, the osmotic potential of which is determined by the concentration of the monomers. It is important that, at a given concentration, the molecular size of the osmoticum is significantly above the cut-off of the membrane. This is given if the molecular weight is above 20 kDa, when using polyvinyl alcohol or polyethylene oxide and ultrafiltration membranes with a molecular size cut-off of 5 nm. For example, polyethylene oxide is well suitable as a high-molecular weight osmoticum for the assay according to the present invention, because with this polymer, which is commercially available in various molecular sizes, a relatively high osmotic pressure (>1 MPa) can be achieved at an arguable viscosity (<500 mPa $s^{-1}$).

As is generally known, solutions of high-molecular weight polyelectrolytes such as polyacrylate, dextran sulfate, polystyrene sulfonate, poly-(diallyldimethylammonium chloride) and others show a strong osmotic force already at low mass concentration, because the electrically absorbed counter ions exist in high particle concentration. The hydraulic effect of the polyelectrolytes on the ultrafiltration membrane is especially high if the salt concentration of the aspirated liquid is low compared to the concentration of the polymer-bound ions of the polyelectrolyte solution. A polymer osmoticum widely applicable for the invention is high-molecular weight sodium dextran sulfate supplied by Pharmacia with an average molecular size of 500 kDa. It is non-permeable for membranes with ultrafiltration features and pore size below 20 nm, it provides concentrated and osmotically high efficient solutions at comparatively low viscosity and it is translucent in the visible and short wave band of radiation.

While water and the low-molecular weight components of the liquid pass the pores of the ultrafiltration membrane and flow into the aspiration chamber, the dissolved high-molecular weigh substances to be detected, e.g. labeled reactants or products of an affinity reaction, are concentrated inside the measuring chamber where its amount can be detected in a very sensitive way by means of radioactivity, optical properties such as fluorescence or luminescence, magnetic or electric properties or a catalytic, e.g. enzymatic activity provided by a label.

To prevent air from penetrating into to the measuring chamber after the filling chamber is completely emptied out, the polymer osmoticum can be added to the reagent in low concentration. Thus the concentration ratio of the labeled macromolecules can be adjusted.

The enrichment of the labeled molecules in a small volume at relatively high layer thickness is an essential advantage of the present invention, particularly for the development of a miniaturized test array. Another important advantage of the method according to the invention consists in the convenient separation of the labeled soluble macromolecules or high-molecular weight complexes from other labeled molecules which can be present in excess. The fraction of labeled molecules to be separated can be prevented from flowing into the measuring chamber by linkage to a surface or a particulate affinity sorbent. Said fraction can also be of low-molecular weight, flowing through the pores of the ultrafiltration membrane into the aspiration chamber together with the water. The former option has the advantage of a positive dose-effect-correlation, whereas the latter option enables an assay in homogeneous phase, thus having the advantage that there is no need for immobilization of any affinity reactant.

To name an example, a definite amount of labeled antibodies can be mixed with a sample matrix containing low-molecular weight analytes. Thereafter, a fraction of the antibodies is linked to the analytes. Subsequently, affinity sorbent competing against the analytes for the antibodies is added in excess amount. Only those labeled antibodies that are linked to the analytes remain in the liquid phase. Subseqently the liquid phase is moved into the measuring chamber. After filling the solution of polymer osmoticum into the aspiration chamber, a large extent of the liquid is soaked from the filling chamber into the measuring chamber where the labeled antibodies linked to the analytes are concentrated. An extensively stoichiometric, positive dose-effect correlation can be achieved.

By the method according to the present invention, a heterogeneous competitive affinity assay with positive dose-effect correlation can also be obtained by a labeled, particle-bound complex according to the displacement principle. The complex consists of an affinity receptor and a high-molecular weight labeled analog of the analyte. The non-labeled fraction of the complex is covalent or physically linked to the surface whereas the labeled fraction can be displaced by ligand substitution with the analyte. In this case it is advantageous if the analyte has a high affinity to the receptor (e.g. an antibody), whereas the labeled analog is bound with medium affinity so that a short reaction time and a virtually stoichiometrical reaction can be expected. After the reaction, the labeled soluble products are concentrated in the measuring chamber. A direct dependence of the signal on the analyte concentration is obtained here, too.

The present invention also enables heterogeneous affinity assays with low-molecular weight labeled analogs at which a positive dose-effect correlation is attained. For example the competition of a low-molecular weight analyte against a low-molecular weight fluorescent analog for an affinity sorbent with immobilized antibodies is used. The liquid phase contains the fluorescent low-molecular weight analog in a concentration directly dependent on the concentration of the analyte. If now the antibody in dissolved form is added in excess amount, the residual soluble marker is transferred into a high-molecular weight complex and can be accumulated inside the measuring chamber. It is also possible that a solution of the unlabeled antibody is introduced into the measuring chamber by use of capillary force before adding the sample and the other reacting components. After the osmotically induced aspiration of the liquid phase, the soluble fraction of the low-molecular weight labeled analog is linked to the antibody and is concentrated inside the measuring chamber.

If the present invention is used for a heterogeneous fluorescence immunoassay with high-molecular weight labeled substances, the measuring of fluorescence is carried out inside an additional measuring chamber after the immune reaction has finished. If the fluorophore is covalently bound to the macromolecule, the fluorescence measurement can be carried out in an environment containing electrolytes optimal for fluorescence, even if the environment is incompatible with the reaction itself. If for instance a fluorescein-labeled reactant is applied, it is reasonable to adjust the pH-value of the solution of the polymer osmoticum to about 9. The mentioned fluorophore can be determined in alkaline environment with very high fluorescence yield.

Using the method according to the present invention, a competitive affinity assay of high sensitivity for low-molecular weight analytes can be carried out in homogeneous phase.

Hereunto, one can apply for example two reagents, at first a non-labeled affinity receptor for the analyte, normally an antibody, and at second a labeled low-molecular weight competing ligand, e.g. a conjugate of the analyte and a fluorescence dye. The assay can be carried out in a way that a restricted and definite amount of the antibody reacts with the analyte initially and adjacently with a labeled low-molecular weight competing ligand that is in excess amount with respect to the antibody. In this way a fraction of the labeled low-molecular weight substance dependent on the amount of the analyte is transferred into the high-molecular weight complex, thus being able to concentrate inside the measuring chamber. If the concentration of the analyte and the competing ligand are far beyond their respective dissociation constants, the quantity of the labeled detectable complex corresponds to the difference of the quantity of the antibody and that of the analyte. The accuracy of this assay can be increased by carrying out pairwise tests with the sample matrix and a blank value on one array. In this case, the difference of the signals positively correlates to the analyte concentration.

A sensitive ratiometric measurement can be carried out by means of the presented homogeneous system. If both the low-molecular weight competing ligand and the high-molecular weight receptor are labeled and both labels can be quantified separately, e.g. due to different fluorescence spectra, it is possible to quantify the fraction linked to the analyte, without parallel samples.

If the present invention is applied for carrying out the homogeneous assay in the described form, it is desirable to completely wash out the labeled competing ligand of low molecular weight. The elution of the low-molecular weight marker fraction from the measuring chamber can be realized by aspiration of additional unlabeled aqueous solution through the ultrafiltration membrane and/or by replacement of the osmotically active polymer solution inside the aspiration chamber. Aspiration of additional unlabeled solution also enables the complete transfer of labeled macromolecules into the measuring chamber. It is eased by placing a hydrophilic filter with a pore size of approx. 2 µm or a bed of fine hydrophilic particles, which is permeable for aqueous solutions of colloids, between the filling and the measuring chamber, thus preventing air from penetrating the measuring chamber.

The present invention also enables miniaturized enzyme linked immunosorbent assays (ELISA). For example, an antibody is used which is linked by covalent binding to an enzyme, e.g. a peroxidase. The fraction of the antibody added in excess amount, which forms a complex with the analyte, cannot bind to the subsequently added particulate affinity sorbent also present in excess amount. In this case the solution of the high-molecular weight osmoticum which is introduced into the aspiration chamber, contains an unlabeled enzyme substrate of low molecular weight, which crosses the ultrafiltration membrane. The enzymatically active complex accumulating by ultrafiltration inside the measuring chamber catalyzes the reaction of the substrate into a colloidal fluorescent or colored substance. The latter is concentrating inside the measuring chamber so that in a little while a highly amplified signal, positively correlated to the analyte concentration, is generated in a small space by utilization of the enzyme reaction.

The present invention can be used in a similar way to carry out a sensitive assay on the basis of a colloidal silver precipitate or another colloidal precipitate. If for example gold-nanoparticles are used for labeling an immune reagent and if they are concentrated inside the measuring chamber according to the present invention, it comes to a precipitation of metallic colloidal silver dependent on the amount of gold particles if the solution of the osmoticum contains a suitable reductive agent and silver ions.

The fluidic micro-system according to the present invention, which is suitable for, but not restricted to, the realization of the aforesaid assays, particularly affinity assays, comprises at least one aspiration chamber (1) and at least one measuring chamber (4), separated by an ultrafiltration membrane (5) from the aspiration chamber, whereas every measuring chamber is connected via a flow path (3) to a filling chamber (2), the volume of the flow path equaling only a small part of that of the filling chamber and the latter exceeding that of the measuring chamber many times over. The volume of the miniaturized measuring chamber is typically not greater than about 2 µl and its surface is typically not greater than about 5 mm$^2$.

A variant of the fluidic microsystem according to the present invention is illustrated in FIG. 1. It constitutes an array of numerous miniaturized filling chambers (2) and measuring chambers (4) within a translucent solid. Both chambers are hydraulically connected by a capillary flow path (3). Each measuring chamber is separated by an ultrafiltration membrane from an aspiration chamber. Each measuring chamber is designed as the lumen of a segment of a capillary membrane with ultrafiltration properties, e.g. a microdialysis fiber that is crossing the aspirating chamber. This has the advantage that the labeled soluble macromolecules are concentrated inside a very small cavity. Here, they are detectable in a very sensitive way by their fluorescence, luminescence or reactivity. If a dye is accumulated inside the measuring chamber by an enzyme-labeled immune reagent, it can generate a noticeable light signal capable for example by a simple light microscope, because of the comparatively long optical path length. A not limiting example is a dialysis fiber with an inner diameter of about 0.2 mm made from regenerated cellulose that is capable for this purpose presents a translucent membrane which is completely impermeable for antibodies. The small cross section of said fiber enables image interpretation by means of a microscope. At a measuring chamber length of 5 mm, a high color depth or a strong fluorescent signal is possible at strong dilution. An especially high sensitivity in the fluorescence affinity assay is achieved if the excitation light is illuminated crosswise and the fluorescence is measured over the cross-section of the hollow fiber. If the excitation is realized by using laser light, it is easy to achieve the same quantum flow within numerous measuring chambers within the illustrated array so that a simultaneous detection is possible. Shall an affinity assay be carried out in inhomogeneous phase, a particle filter between filling and measuring chamber can be provided to prevent affinity sorbent of even small particle size from flowing into the measuring chamber.

The form of implementation of the appliance according to the present invention shown in FIG. 1 is not the only possible form. It can be beneficial for particular applications or for the cost-effective production of the array if the hollow fiber segments are arranged parallel to the array plane or if planar ultrafiltration membranes are applied instead of capillary membranes. For example the array can consist of two corpora with an ultrafiltration membrane pasted inbetween. In this case, aspiring chambers, filling chambers, flow paths and measuring chambers are constituted by channels or cavities embedded in these corpora.

FIG. 2 shows the array in a section across a unity of filling chambers (2) and measuring chambers (4). Each measuring chamber is formed by a narrow, vertically running channel. The aspiration chamber (1) is constituted by a wide channel embedded in the opposite corpus, running vertically to the cross-section. It is separated from the measuring chamber by an ultrafiltration membrane.

For the coverage of ligands by means of their radioactivity using an x-ray film it is advantageous if a very shallow measuring chamber is used which is separated from the aspiration chamber by the ultrafiltration membrane on one side and bordered by a thin liquid-impermeable membrane adjacent to the x-ray film on the other side.

Other variants of design of assays according to the present invention, particularly affinity assays and fluidic micro-systems, are possible depending on the type of used reactants and/or affinity conjugation partners as well as the type of used detection methods, and are easily to be realized by experts through modification of the described general principles of composition.

EXAMPLE

A fluorescence-labeled protein was concentrated inside a fluidic micro-system according to the present invention within the observing area of a fluorescence microscope. The increase of fluorescence intensity was observed with a fluorescence microscope.

The micro-system comprised two micro-chambers that were connected by microdialysis fibers made from regenerated cellulose (inner diameter 240 µm). One open end of the capillary dialysis membrane was situated inside the first chamber representing the filling chamber whereas the second chamber, representing the aspirating chamber, was crossed by a hollow fiber segment (the measuring chamber), the open end of which was communicating to the atmosphere outside the chamber. This means that the wall of the dialysis hollow fiber formed the ultrafiltration membrane while its lumen provided both the flow path and the measuring chamber. After filling 5 µl of a diluted polymer solution (10 mM sodium phosphate, pH 7, with 0.1% sodium dextran sulfate) into the filling chamber and into the aspiration chamber, the lumen of the capillary membrane (100 nl) was filling up by adhesion. Fluorescein-labeled immunglobuline in strong dilution was added to the filling chamber, so that the fluorescence intensity was at the detection limit. Adjacently the diluted buffered polymer solution inside the aspiration chamber was replaced by a concentrated solution of sodium dextran sulfate (20%) with an osmotic pressure of approx. 30 bar. By this, it was possible to draw the most part of the fluid from the filling chamber into the aspiration chamber within 30 minutes and to concentrate the fluorescence-labeled immunglobuline within the lumen of the hollow fiber segment. Now the fluorescent activity was clearly recognizable with the fluorescence microscope. The flow was automatically terminated and the hollow fiber lumen did not run dry because sodium dextran sulfate was simultaneously concentrated inside the hollow fiber segment.

What is claimed is:

1. A method of affinity assay for analytes that are affinity reactants comprising:
   introducing a high-molecular weight osmoticum solution into at least one aspiration chamber (1), wherein the aspiration chamber is bordered by an ultrafiltration membrane (5), thereby moving a liquid phase out of a filling chamber (2) through a flow path (3) into a measuring chamber (4), the measuring chamber being separated from the aspiration chamber by the ultrafiltration membrane, wherein the flow path connects the filling chamber to the measuring chamber, whereby due to a reaction of the analyte with another affinity reactant the liquid phase comprises labeled high molecular weight affinity reactants or reaction products of the analyte in analyte-dependent concentration,
   the labeled affinity reactants or reaction products being labeled with a functional group allowing a sensitive determination of their quantity;
   concentrating the high-molecular weight labeled affinity reactants or reaction products to be detected inside the measuring chamber;
   detecting the high-molecular weight labeled reactants or reaction products inside the measuring chamber; and
   flowing the liquid phase with low-molecular weight constituents through pores of the ultrafiltration membrane into the aspiration chamber.

2. The method of affinity assay according to claim 1, wherein the high-molecular weight osmoticum is selected from the group consisting of polyvinyl alcohol, polyethylene oxide, polystyrene sulfonate, poly(diallyldimethylammonium chloride), a dextran sulfate, and a polyacrylate.

3. The method of affinity assay according to claim 1, further comprising detecting the labeled high-molecular weight reactants or reaction products inside the measuring chamber by a process selected from the group consisting of direct optical interaction, radioactivity, magnetic properties, electric properties, enzymatic reaction marker(s), and catalytic chemical reaction marker(s).

4. The method of affinity assay according to claim 1, wherein the affinity reactants reacting with the analyte are selected from the group consisting of antibodies, antigens, lectins and aptamers.

5. The method of affinity assay according to claim 1, wherein the liquid phase further comprises high-molecular weight nonlabeled affinity receptors for the analyte and low-molecular weight labeled analogs that compete against the analyte, wherein a fraction of the analogs, the fraction being dependent on the analyte concentration, is linked to the affinity receptors and concentrated inside the measuring chamber.

6. The method of affinity assay according to claim 1, wherein after the reaction the filling chamber contains immobile reactants or analogs of the analyte to which a fraction of the labeled reactants or reaction products is linked and wherein the fraction of the labeled reactants or reaction products is dependent upon the concentration of the analyte and is prevented from flowing into the measuring chamber.

7. The method of affinity assay according to claim 1, wherein the reactants or reaction products concentrated inside the measuring chamber incorporate fluorophores having a fluorescence yield increased by electrolytes filled into the aspiration chamber together with osmotically, hydraulically effective polymers.

8. The method of affinity assay according to claim 1, wherein the reactants or reaction products concentrated inside the measuring chamber show an enzymatic activity and a colloid product is formed by enzymatic reaction from a low-molecular weight substrate diffusing out of the aspiration chamber into the measuring chamber.

9. The method of affinity assay according to claim 1, wherein at least one of the reactants or reaction products concentrated inside the measuring chamber incorporates one or more catalysts for a precipitating reaction and the solution of the high-molecular weight osmoticum in the aspiration chamber includes one or more reactants for the catalyzed precipitating reaction.

10. The method of affinity assay according to claim 9, wherein the catalysts are gold nanoparicles and the reactants are silver ions and a reductive agent.

* * * * *